United States Patent
Watanabe et al.

(10) Patent No.: US 7,306,712 B2
(45) Date of Patent: Dec. 11, 2007

(54) GAS SENSOR AND METHOD FOR MEASURING GAS CONCENTRATION USING THE SAME

(75) Inventors: Masaya Watanabe, Aichi (JP); Norihiko Nadanami, Aichi (JP); Tomonori Kondo, Aichi (JP); Ryuji Inoue, Gifu (JP); Takafumi Oshima, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 219 days.

(21) Appl. No.: 10/144,835

(22) Filed: May 15, 2002

(65) Prior Publication Data

US 2003/0066763 A1    Apr. 10, 2003

(30) Foreign Application Priority Data

May 15, 2001  (JP)  ............................. 2001-145299
Oct. 25, 2001  (JP)  ............................. 2001-327477

(51) Int. Cl.
   *G01N 27/407*   (2006.01)
(52) U.S. Cl. ........................ 205/784; 204/424; 204/426
(58) Field of Classification Search ................ 204/401, 204/412, 424, 426, 431; 205/775.5, 784, 205/785.5; 73/23.31; 340/632, 634; 422/94
   See application file for complete search history.

(56) References Cited

U.S. PATENT DOCUMENTS

| | | | | |
|---|---|---|---|---|
| 4,498,968 A | * | 2/1985 | Yamada et al. | ............. 204/412 |
| 4,990,235 A | * | 2/1991 | Chujo | ........................ 204/424 |
| 5,215,643 A | * | 6/1993 | Kusanagi et al. | ........... 204/412 |
| 5,298,147 A | * | 3/1994 | Nakae et al. | ................ 204/424 |
| 5,302,274 A | | 4/1994 | Tomantschger et al. | |
| 5,453,172 A | * | 9/1995 | Alberti et al. | .............. 204/421 |
| 6,068,748 A | | 5/2000 | Berger et al. | |
| 6,238,535 B1 | * | 5/2001 | Taniguchi et al. | .......... 204/424 |
| 6,652,723 B1 | | 11/2003 | Nadanami et al. | |

FOREIGN PATENT DOCUMENTS

| | | |
|---|---|---|
| EP | 0 330 249 A2 | 8/1989 |
| EP | 1 037 041 A2 | 9/2000 |
| EP | 1 103 807 A2 * | 5/2001 |
| JP | 7-31153 | 4/1995 |
| JP | 2001-215214 A | 8/2001 |
| WO | 01/25777 A1 | 4/2001 |

OTHER PUBLICATIONS

Keiich Saji, Characteristics of Limiting Current-Type Oxygen Sensor, Oct. 1987, Journal of the Electrochemical Society, vol. 134, No. 10, 2430-2435.*
Aldrich Chemical Company, Inc. Catalog of Chemicals, 1996-1997, p. 1054.*
Japanese Office Action dated May 17, 2005.

* cited by examiner

*Primary Examiner*—Kaj K. Olsen
(74) *Attorney, Agent, or Firm*—Sughrue Mion, Pllc.

(57) ABSTRACT

This invention provides a gas sensor including a proton-conductive polymer electrolyte layer and a method for measuring gas concentration, that are capable of measuring gas concentration at high accuracy notwithstanding the presence of water vapor.

9 Claims, 4 Drawing Sheets

GAS SENSOR AND METHOD FOR MEASURING GAS CONCENTRATION USING THE SAME

FIELD OF THE INVENTION

The present invention relates to gas sensor and to a method for measuring gas concentration by use of the same. More particularly, the invention relates to a gas sensor and a method for measuring gas concentration that are capable of measuring the concentration of a gas to be measured on the basis of a limiting current flowing between electrodes formed on a proton-conductive polymer electrolyte element. The present invention further relates to a combustible-gas sensor which is adapted to measure the concentration of a combustible gas, such as hydrogen gas, which is contained in a fuel gas, such as methanol-reformed gas for use in a fuel cell, and which is suitably used for measurement or control of hydrogen gas concentration.

BACKGROUND OF THE INVENTION

In response to concerns about global environmental pollution, in recent years intensive studies have been conducted on fuel cells for use as highly-efficient, clean power sources. Among such fuel cells, a polymer electrolyte fuel cell (PEFC) shows promise for fuel cells for automobile use, by virtue of its advantages, such as operation at low temperature and high output density. A promising fuel gas for use in PEFC is a reformed gas reformed from methanol or the like. In this connection, in order to enhance efficiency, etc., a sensor capable of direct detection of a combustible gas, such as hydrogen, contained in a reformed gas is required. Since the above-described sensor is exposed to a hydrogen-rich atmosphere, it must operate at low temperature (about 100° C. or less). Japanese Patent Publication (kokoku) No. 7-31153 proposes such a low-temperature operation type sensor. This sensor is configured such that a working electrode, a counter electrode, and a reference electrode are disposed on an insulating base material while the three electrodes are unitarily covered with a gas permeable proton conductor membrane.

The sensor disclosed in the above-described patent publication uses, as a proton conductor, Nafion (registered trademark, product of DuPont), which is one type of fluorine-containing resin and is used in polymer electrolyte fuel cells.

However, when protons travel through the above-described proton conductor such as Nafion, the protons travels together with $H_2O$ molecules. Further, the quantity of $H_2O$ molecules which accompany the traveling protons changes depending on the $H_2O$ concentration of an atmosphere. Therefore, the sensor output of a gas sensor using a proton conductor such as Nafion changes with the $H_2O$ concentration. Thus, in measurement in the presence of water vapor, no known gas sensors and methods for measuring gas concentration can measure hydrogen gas concentration without problems due to the influence of water vapor.

SUMMARY OF THE INVENTION

An object of the present invention is to solve the above-described problems, and to provide a gas sensor and a method for measuring gas concentration which measure the gas concentration by measuring a limiting current flowing between electrodes formed on a proton-conductive polymer electrolyte element and which, even when water is present in an atmosphere to be measured, can measure the concentration of a gas contained in the atmosphere while overcoming problems due to the influence of water vapor.

In accordance with the present invention, the problem of overcoming the adverse affects of water vapor on the gas measurement is achieved by providing a gas sensor comprising a gas sensor comprising a proton conductive-polymer electrolyte layer; a first electrode and a second electrode provided in contact with the proton-conductive polymer electrolyte layer; a partition wall or gas diffusion controlling portion provided between the first electrode and the gas atmosphere to be measured; and the gas sensor further comprises at least one of the following:

(1) a diffusion-controlling hole provided in the partition wall and extending through the partition wall between the first measuring electrode and the atmosphere to be measured, the gas sensor being characterized in that $A/(B \times C)$ is not less than $9.5 \times 10^{-5}$ $mm^{-1}$, where $A$ ($mm^2$) is an opening area of the diffusion-controlling hole on a side toward the gas atmosphere to be measured, $B$ (mm) is a length of the diffusion-controlling hole, and $C$ ($mm^2$) is an area of the first electrode or that of the second measuring electrode, whichever is smaller, and (2) the proton-conductive polymer electrolyte layer is formed of a polymer electrolyte having a thickness of not less than 0.08 mm.

Furthermore, a method for measuring a gas concentration is provided comprising measuring a limiting current flowing between the first electrode and a second electrode by use of the gas sensor as described above.

The gas sensor of the present invention in one preferred aspect comprises a proton-conductive polymer electrolyte layer, a first measuring electrode and a second measuring electrode formed in contact with the polymer electrolyte layer, a partition wall provided between the first measuring electrode and an atmosphere to be measured, and a diffusion-controlling hole provided in the partition wall and extending through the partition wall between the first measuring electrode and the atmosphere to be measured. The gas sensor is characterized in that $A/(B \times C)$ is not less than $9.5 \times 10^{-5}$ $mm^{-1}$, where $A$ ($mm^2$) is the opening area of the diffusion-controlling hole on the side toward the atmosphere to be measured, $B$ (mm) is the length of the diffusion-controlling hole, and $C$ ($mm^2$) is the area of the first measuring electrode or that of the second measuring electrode, whichever is smaller.

In another preferred aspect, a combustible-gas sensor according to the present invention has a proton conductive layer formed of a polymer electrolyte having a thickness of not less than 0.08 mm. In this embodiment, since the proton conductive layer is formed to have a sufficiently large thickness, when the $H_2O$ concentration of an atmosphere changes, the quantity of $H_2O$ molecules which accompany protons traveling through the proton conductive layer changes to a reduced degree. In other words, when the thickness of the proton conductive layer increases, the proton conductive layer becomes less susceptible to variation in $H_2O$ concentration. Therefore, the $H_2O$ dependency of combustible-gas concentration measurement can be reduced.

Also, in a combustible-gas sensor according to a further preferred embodiment of this aspect of the present invention, the proton conductive layer is formed of a polymer electrolyte wherein protons of ion exchange groups of the polymer electrolyte have been partially substituted by metal ions.

Figure 1:
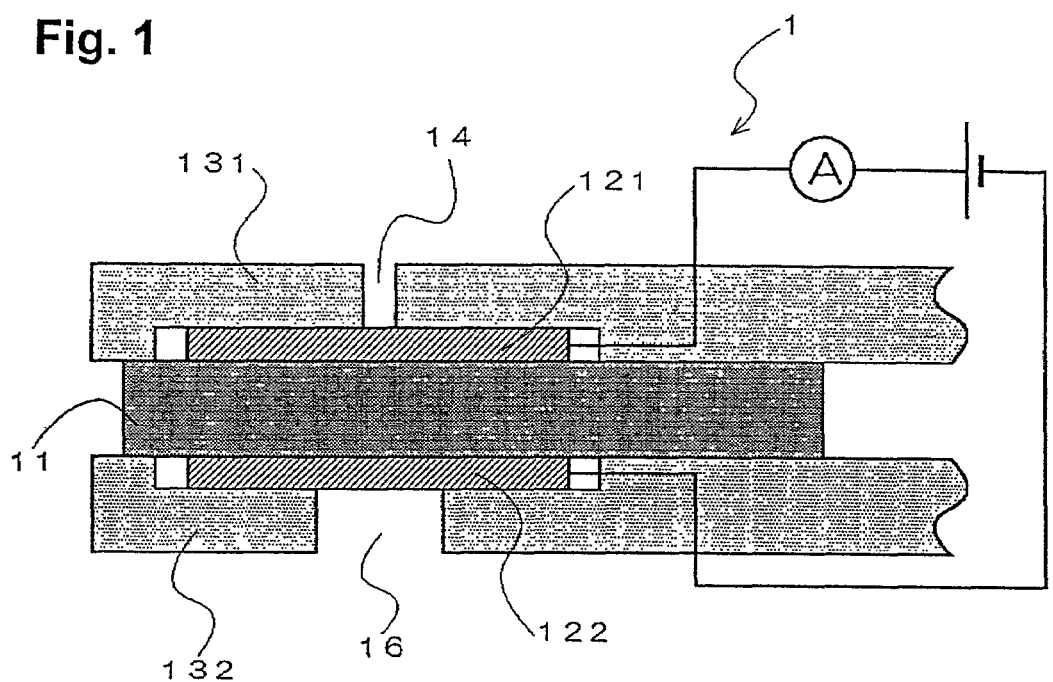
FIG. 1 is a schematic sectional view showing an example of a gas sensor of the present invention.
Figure 2:
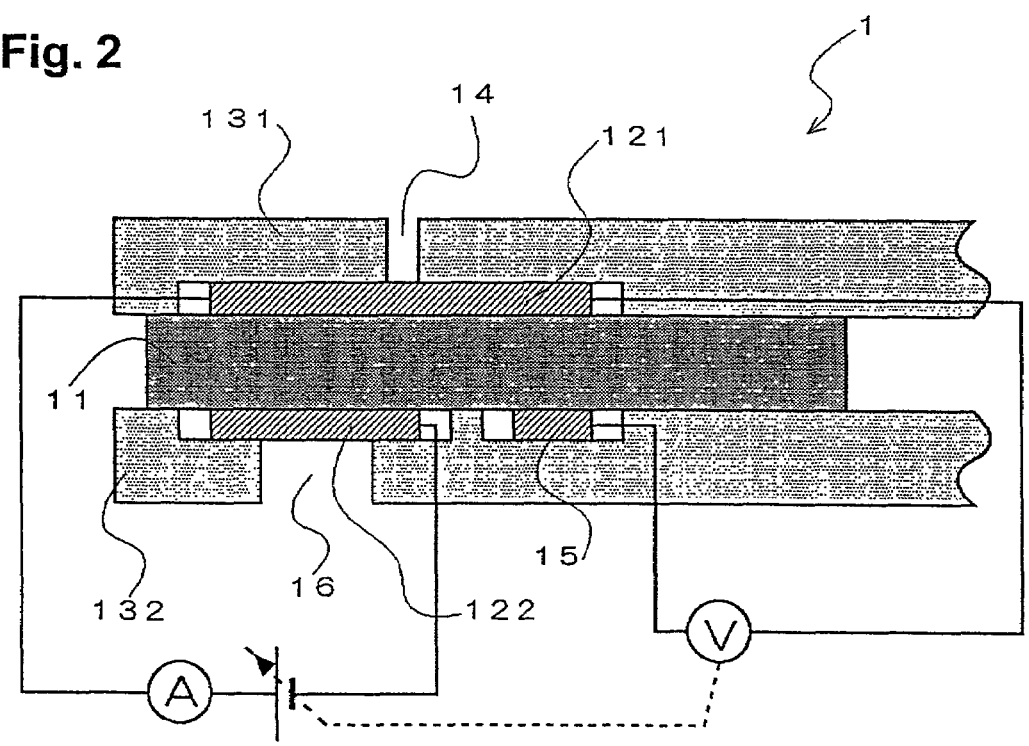
FIG. 2 is a schematic sectional view showing another example of a gas sensor of the present invention.
Figure 3:
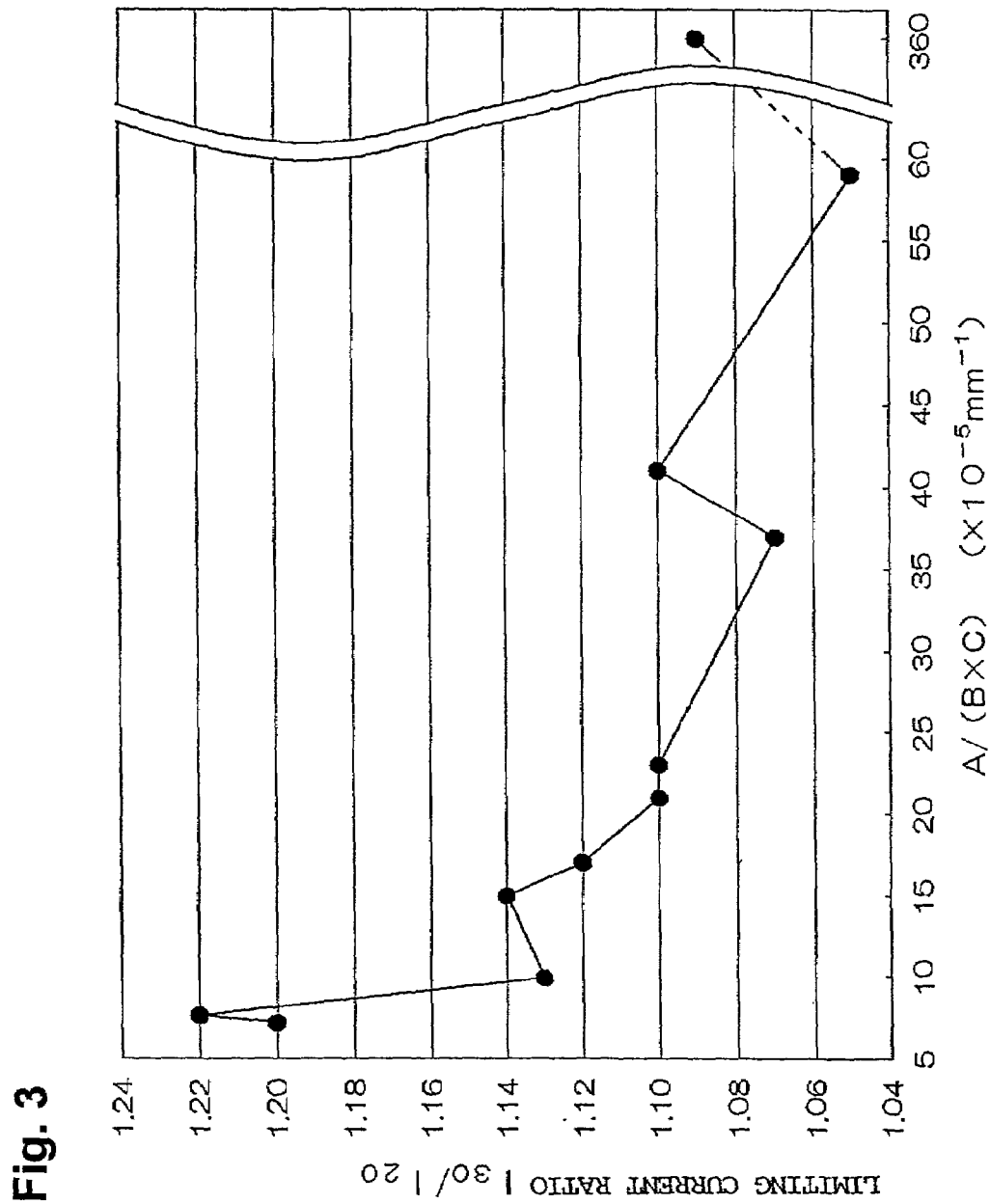
FIG. 3 is a graph showing the interrelation between $A/(B \times C)$ and $I_{30}/I_{20}$.

The reference numerals in the drawings are defined below:

1: gas sensor
11: polymer electrolyte layer
121: first electrode (first measuring electrode)
122: second electrode (second measuring electrode)
131: substrate for the first measuring electrode side (partition wall)
132: substrate for the second measuring electrode side
14: diffusion-controlling hole
15: reference electrode
16: outlet
201a: upper support element
201b: lower support element
202: proton conductive layer
203: first electrode (first measuring electrode)
204: second electrode (second measuring electrode)
205: reference electrode
206: gas diffusion controlling portion
207, 209: power supply
208: ammeter
210: potentiometer
211: hole

DETAILED DESCRIPTION OF THE INVENTION

The polymer electrolyte layer in the present invention is particularly formed of a proton-conductive polymer electrolyte. Preferably, such a polymer electrolyte is of a fluorine-containing resin type. A polymer electrolyte of a fluorine-containing resin type can be operated at low temperature (room temperature to 130° C.). Preferably, among such polymer electrolytes, Nafion (registered trademark, product of DuPont) is used.

The polymer electrolyte layer may vary in size, thickness, shape, etc. However, when the first electrode and the second electrode are to be provided on the respective opposite sides of the polymer electrolyte layer, the polymer electrolyte layer preferably has a thickness of 30-600 µm (more preferably 90-360 µm).

The above-mentioned "first electrode" is used for measuring and is a porous electrode formed in contact with the polymer electrolyte layer. The first electrode is isolated from the atmosphere to be measured by a partition wall, and is allowed to come into contact with a gas to be measured (an object of measurement contained in an atmosphere to be measured) only through a diffusion-controlling hole. The first electrode may be in contact with the partition wall or may be separated from the partition wall. The first electrode is connected via a power supply to a second electrode, described below, whereby voltage is applied thereto. The thus-arranged first electrode is adapted to decompose a predetermined gas to be measured which is contained in the atmosphere to be measured and reaches the same through the diffusion-controlling hole.

The above-mentioned "second electrode" is used for measuring and is a porous electrode formed in contact with the polymer electrolyte layer and usually opens (partially or entirely) upon the atmosphere or an atmosphere to be measured. Thus, protons transmitted from the first electrode through the polymer electrolyte layer are formed into hydrogen gas at the second electrode, and the thus-formed hydrogen gas can be ejected from the second electrode. The first electrode and the second electrode may be formed on the same side or on the respective opposite sides of the polymer electrolyte layer.

No particular limitations are imposed on the area of the first electrode and that of the second electrode. However, each of the first and second electrodes usually assumes an area of 6-27 mm². Thus, when, as mentioned above, "C" represents the area of the first electrode or that of the second electrode, whichever is smaller, a preferred value of "C" is the above-mentioned preferred area. As will be described later, the first electrode and the second electrode usually assume the form of a very thin layer. The term "area" appearing herein refers to the area of the surface of an electrode.

In accordance with a first embodiment, no particular limitations are imposed on the thickness of the first electrode and that of the second electrode. Preferably, each of the first and second measuring electrodes has a thickness of 200-600 µm.

The above-mentioned "reference electrode" is adapted to function in the following manner. In order to measure a reference electric-potential difference which serves as a reference for voltage to be applied between the first electrode and the second electrode, the reference electric-potential difference is induced between the reference electrode and the first electrode.

Preferably, the first electrode, the second electrode, and the reference electrode each include a catalyst layer and a gas diffusion layer. Preferably, the catalyst layer is constituted of a composite formed such that carbon particles which carry platinum or platinum alloy on their surfaces are covered with a polymer electrolyte. Preferably, the gas diffusion layer is formed of carbon paper and/or carbon cloth. Usually, as viewed from the polymer electrolyte layer, the gas diffusion layer is formed on the far side of an electrode, and the catalyst layer is formed on the near side of the electrode.

The above-mentioned "partition wall" is adapted to prevent entry of an atmosphere to be measured into the first measuring electrode from a portion other than that corresponding to the diffusion-controlling hole, described below, and is preferably formed of a gas-impermeable, dense sintered body. The thickness of the partition wall is not particularly limited, but is preferably 0.5-2 mm.

The above-mentioned "diffusion-controlling hole" is a through-hole formed in the partition wall. No particular limitations are imposed on the size, shape, quantity, etc. in relation to the diffusion-controlling hole. Preferably, "A," which, as mentioned above, represents the opening area of the diffusion-controlling hole (a total area when a plurality of diffusion-controlling holes are formed) on the side toward an atmosphere to be measured, is smaller in value than "C," which represents the area of an electrode, and A/C is $5.0 \times 10^{-5}$ to $5.0 \times 10^{-3}$.

As mentioned above, "B" represents the length of the diffusion-controlling hole. The value of B is not particularly limited, but is usually 0.5-1.2 mm.

The above-mentioned "A/(B×C)" is preferably not less than $9.5 \times 10^{-5}$ mm$^{-1}$. When "A/(B×C)" is less than $9.5 \times 10^{-5}$ mm$^{-1}$, the ratio $I_{30}/I_{20}$ becomes 1.2 or greater, where $I_{30}$ is a limiting current as measured with an atmosphere to be measured which contains $H_2$ in an amount of 50% by volume and $H_2O$ in an amount of 30% by volume, and $I_{20}$ is a limiting current as measured with an atmosphere to be measured which contains $H_2$ in an amount of 50% by volume and $H_2O$ in an amount of 20% by volume. This means that, when atmospheres to be measured contain $H_2$ at the same concentration but exhibit a 10% difference in $H_2O$ concentration, a difference of 10% or greater arises between measured values in measurement with the atmospheres. This is unfavorable.

According to the gas sensor of a one embodiment of the present invention, employment of an "A/(B×C)" value not less than $9.5 \times 10^{-5}$ mm-1 can limit the $I_{30}/I_{20}$ value to less than 1.2. That is, the difference in measured values can be less than 10% between an atmosphere to be measured which contains $H_2$ in an amount of 50% by volume and $H_2O$ in an amount of 30% by volume and an atmosphere to be measured which contains $H_2$ in an amount of 50% by volume and $H_2O$ in an amount of 20% by volume.

The reason why the selection of a certain range of the "A/(B×C)" value renders measurement less susceptible to the influence of water vapor is uncertain, but a conceivable reason is as follows. By increasing the diffusion resistance index per unit electrode area (A/B), the degree of diffusion control is reduced (diffusion is facilitated) in relation to entry of an atmosphere to be measured into the first electrode through the diffusion-controlling hole; and by increasing a current flowing between the first electrode and the second electrode, more protons are caused to be transmitted through the polymer electrolyte layer, whereby the amount of water molecules entering the polymer electrolyte layer is increased. In this manner, the amount of water molecules passing through clusters, which are ion conductive paths in the polymer electrolyte layer, can be limited, whereby the influence of water vapor can be reduced.

Next are discussed embodiments of the invention wherein gas measurement problems due to the presence of water vapor are overcome by adjusting the thickness and other characteristics of the proton-conductive polymer electrolyte layer.

When protons of ion exchange groups of the polymer electrolyte are partially substituted by metal ions, the EW (=1000/ion exchange group capacity) increases. The increased EW reduces the quantity of $H_2O$ molecules which accompany protons traveling through the proton conductive layer. Therefore, when the $H_2O$ concentration of an atmosphere changes, the quantity of $H_2O$ molecules which accompany the protons changes to a reduced degree. As a result, the $H_2O$ dependency of combustible-gas concentration measurement can be reduced. For example, the $H_2O$ dependency of combustible-gas concentration measurement can be reduced through employment of a proton conductive layer formed of a polymer electrolyte, protons of ion exchange groups of the polymer electrolyte having been partially substituted by sodium ions. Notably, the proton conductive layer preferably has an EW (=1000/ion exchange group capacity) of not less than 1100. EW is defined by $EW=1000/q$ [q (meq/g): ion exchange group capacity] and is obtained by acid-base neutralization titration.

Another preferred mode for carrying out the present invention is next described.

In this preferred mode of the present invention, protons of ion exchange groups of a polymer electrolyte, which constitute the proton conductive layer, are partially substituted by ions which can be exchanged with protons of ion exchange groups of the proton conductive layer; for example, by potassium ions or copper ions, and particularly preferably by sodium ions.

In this preferred mode of the present invention, protons of ion exchange groups of a polymer electrolyte, which constitute the proton conductive layer, are substituted by use of an aqueous solution containing metal ions at a concentration not greater than $10^{-3}$ mol/L.

In this preferred mode of the present invention, the combustible-gas sensor has a reference electrode provided in contact with the proton conductive layer; and a predetermined voltage is applied between the first electrode and the second electrode in such a manner as to establish a constant electric potential difference between the first electrode and the reference electrode.

In this preferred mode for carrying out the present invention, the first electrode and the second electrode are formed in opposition to each other with the proton conductive layer being held therebetween. This configuration reduces resistance between the first and second electrodes, thereby enhancing the proton conductive capability of the proton conductive layer. Notably, when gas diffusion resistance of a gas diffusion controlling portion increases excessively, the sensitivity of the combustible-gas sensor drops. Therefore, when sensitivity must be held at a certain, appropriate level, the area of the first electrode and/or the area of the second electrode is preferably increased. When sufficient sensitivity can be attained, the first electrode and the second electrode can be formed on the same plane of the proton conductive layer.

Another preferred aspect for carrying out the present invention uses a proton conductive layer which is formed of a polymer electrolyte and operates sufficiently at relatively low temperature; for example, not higher than 150° C., preferably not higher than 130° C., more preferably around 80° C., such as a proton conductive layer formed of a resin-type solid polymer electrolyte.

In another preferred mode for carrying out the present invention, each electrode is a porous electrode which is made mainly of carbon or the like and carries a catalyst, such as Pt, on the side in contact with the proton conductive layer.

In a further preferred mode for carrying out the present invention, each electrode is formed such that a layer containing a polymer electrolyte is formed on the side in contact with the proton conductive layer (interface between the electrode and the proton conductive layer) through application of a solution containing a polymer electrolyte similar to the proton conductive layer. As a result, the contact area between the proton conductive layer and a catalytic component carried by the electrode increases, thereby further enhancing the proton conductive capability.

According to another preferred aspect for carrying out the present invention, the proton conductive layer, the electrodes, and a gas diffusion controlling portion are supported by a support element to thereby configure a unitary combustible-gas sensor. The support element is formed of an inorganic insulator, such as alumina ceramic, or an organic insulator made of resin or a like material. The gas diffusion controlling portion is preferably formed of a gas permeable, porous alumina ceramic or a like material or may be configured such that one or more bores having a small cross-sectional area; for example, one or more through-holes each having a very small diameter, are formed in a portion of the support element formed of a dense material. Such a fine through-hole can be formed by use of, for example, a laser beam machining process or an ultrasonic machining process. When a laser beam machining process is used, the diameter of an opening may be adjusted by controlling the diameter of a laser beam, laser output, laser beam emission time, or a like parameter. When a combustible gas contained in a measurement gas is hydrogen, the average pore diameter of the above-mentioned porous material or the diameter of a through-hole(s) is preferably not less than 1 µm, whereby gas diffusion proceeds outside the region of Knudsen diffusion and thus pressure dependence can be reduced.

A combustible-gas sensor according to the present invention is favorably used for measuring the concentration of a combustible gas, particularly, hydrogen gas which is contained in a measurement gas atmosphere containing methanol, particularly for measuring the concentration of a combustible gas, particularly, hydrogen gas which is contained in a fuel gas, particularly a methanol-reformed gas, for use in a fuel cell.

A method for measuring gas concentration of the present invention is characterized by measuring a limiting current flowing between the first measuring electrode and the second measuring electrode using the gas sensor of the present invention.

The measuring method of the present invention employs the following measuring principle. A gas to be measured flows through the diffusion-controlling hole formed in the gas sensor of the present invention and reaches the first electrode, at which the gas is dissociated into ions, including protons. The protons are transmitted to the second electrode through the polymer electrolyte layer. In the second electrode, the protons are formed into hydrogen, which is diffused (ejected) into an atmosphere to be measured or a like atmosphere. At this time, current flowing between the first electrode and the second electrode becomes a limiting current since a sufficient voltage is applied. The limiting current is proportional to the concentration of a gas to be measured contained in an atmosphere to be measured. Thus, the concentration of the gas to be measured can be measured.

The "limiting current" is defined as follows. When the gas sensor is placed in an atmosphere to be measured and the voltage applied between the first electrode and the second electrode is increased gradually, the current as measured between the first electrode and the second electrode becomes substantially constant (with a variation of ±0.2 mA) regardless of the magnitude of the applied voltage. The constant current at that time is called a limiting current.

Preferably, in the measuring method of the present invention, a limiting current flowing between the first electrode and the second electrode is measured while voltage is applied between the first electrode and the second electrode such that voltage as measured between the first electrode and the reference electrode becomes constant.

EXAMPLES

The present invention will next be specifically described by way of example.

[1] Manufacture of Gas Sensors (1) Manufacture of Polymer Electrolyte Layers, First Measuring Electrodes, and Second Measuring Electrodes A sheet formed of Nafion 117 (product of DuPont) was cut into pieces of a predetermined size, thereby obtaining polymer electrolyte layers. Next, a slurry which contains carbon particles carrying platinum fine particles was applied onto the surface of a carbon sheet (400 µm thick), followed by drying. Next, liquid Nafion 117 (product of DuPont) was applied onto the dried carbon sheet, followed by drying. The thus-prepared carbon sheet was cut into pieces of a predetermined size, thereby obtaining electrodes. The thus-obtained electrodes were placed on either side of each of the above-obtained polymer electrolyte layers, followed by hot pressing. Thus were provided polymer electrolyte layers each having the first measuring electrode and the second measuring electrode bonded thereto.

(2) Manufacture of Substrates

A slurry which contains an alumina powder was prepared. The slurry was formed into a green sheet by a doctor blading process. Next, a green pattern of leads for the first measuring electrodes was printed on the green sheet at a predetermined position by use of an electrically conductive paste. Then, the green sheet was cut into pieces of a predetermined size, thereby obtaining green substrates. The green substrates were fired, and then a through-hole of a predetermined diameter was formed in each of the fired substrates at a predetermined position, thereby obtaining substrates (partition walls) for the first measuring electrode side. The thus-obtained substrates for the first measuring electrode side have three kinds of thickness (0.52 mm, 0.79 mm, and 1.18 mm), a longitudinal dimension of 7 mm, a lateral dimension of 40 mm, and a diffusion-controlling hole of a diameter shown in Table 1.

Similarly, green substrates each having a through-hole of a 2 mm diameter and a green pattern were fired, thereby obtaining substrates for the second electrode side. The thus-obtained substrates for the second electrode side have a thickness of 180 µm, a longitudinal dimension of 7 mm, a lateral dimension of 40 mm, and an outlet of a 1.7 mm diameter.

TABLE 1

| | | Diffusion-controlling hole Diameter (mm) | Diffusion-controlling hole Opening area ($\times 10^{-4}$ mm$^2$) | Diffusion-controlling hole Length (mm) | Smaller electrode area (mm$^2$) | A/(B × C) ($\times 10^{-5}$ mm$^{-1}$) | Limiting current ratio $I_{30}/I_{20}$ |
|---|---|---|---|---|---|---|---|
| Compar. examples | 1 | 0.044 | 15 | 1.18 | 18 | 7.2 | 1.20 |
| | 2 | 0.031 | 7.6 | 0.79 | 13 | 7.6 | 2.22 |
| Examples | 1 | 0.052 | 21 | 1.18 | 18 | 9.9 | 1.13 |

TABLE 1-continued

| | Diffusion-controlling hole Diameter (mm) | Diffusion-controlling hole Opening area (×10⁻⁴ mm²) | Diffusion-controlling hole Length (mm) | Smaller electrode area (mm²) | A/(B × C) (×10⁻⁵ mm⁻¹) | Limiting current ratio $I_{30}/I_{20}$ |
|---|---|---|---|---|---|---|
| 2 | 0.035 | 9.6 | 0.52 | 13 | 15 | 1.14 |
| 3 | 0.069 | 37 | 1.18 | 18 | 17 | 1.12 |
| 4 | 0.062 | 30 | | 12 | 21 | 1.10 |
| 5 | 0.079 | 49 | | 18 | 23 | 1.10 |
| 6 | 0.100 | 78 | | | 37 | 1.07 |
| 7 | 0.061 | 29 | | 6 | 41 | 1.10 |
| 8 | 0.126 | 120 | | 18 | 59 | 1.05 |
| 9 | 0.311 | 760 | | | 360 | 1.09 |

(3) Assembly

Platinum wires were connected to the corresponding lead patterns formed on the substrates for the first and second electrode sides, which substrates had been obtained above in (2). Next, each of the polymer electrolyte layers having electrodes, which polymer electrolyte layers had been obtained above in (1), was sandwiched between each of the substrates for the first electrode side and each of the substrates for the second electrode side such that the lead patterns abut the corresponding electrodes. The thus-assembled units were fixated, thereby obtaining 11 kinds of gas sensors.

The thus-obtained 11 kinds of gas sensors had the following dimensions.

Polymer electrolyte layer: thickness about 180 μm; length 13-25 mm; width 3.8-7.2 mm First electrode: thickness about 400 μm; area 3×2=6 mm², 3×4=12 mm², 5.3×2.4=12.7 mm², or 3×6=18 mm²

Second electrode: the same size as that of the corresponding first electrode

Substrate for the first electrode side: thickness 0.52 mm, 0.79 mm, or 1.18 mm

Substrate for the second electrode side: thickness 1.8 mm

[2] Evaluation

Each of the gas sensors obtained above in [1] was fixed such that the detection portion (the polymer electrolyte element, the first electrode, and the second measuring electrode) projects into a chamber. A power supply for supplying variable voltage and an ammeter were connected to platinum wires extending from the first and second electrodes.

Subsequently, a model gas was introduced into the chamber at a flow rate of 10 liters per minute, while the chamber was maintained at 80° C. The model gas contained hydrogen in an amount of 50% by volume, carbon dioxide in an amount of 15% by volume, water in an amount of 20% by volume, and the balance nitrogen. In this state, a voltage of 0-1000 mV was applied between the first measuring electrode and the second measuring electrode, and the limiting current $I_{20}$ was measured. Similarly, the limiting current $I_{30}$ was measured under the same conditions as those in measurement of $I_{20}$ except that a model gas to be introduced into the chamber contains water in an amount of 30% by volume. The limiting current ratio $I_{30}/I_{20}$ was calculated from the thus-measured values. The calculation results are shown in Table 1.

Results

As is apparent from the results shown in Table 1, when A/(B×C) is not less than 9.5×10⁻⁵ mm⁻¹, the limiting current ratio $I_{30}/I_{20}$ can assume a value less than 1.2. This means that, even when the $H_2O$ concentration varies between 20% by volume and 30% by volume in an atmosphere to be measured whose $H_2$ concentration is 50% by volume, the $H_2$ concentration can be measured with an error within 10% by volume.

Thus, even when water is present in an atmosphere to be measured, a gas sensor of the present invention and a method for measuring gas concentration by use of the gas sensor can measure the concentration of a gas to be measured, at high accuracy, through reduction of influence of the water.

Further embodiments of the present invention are next described, with further reference to the drawings.

Example 10

Figure 4:
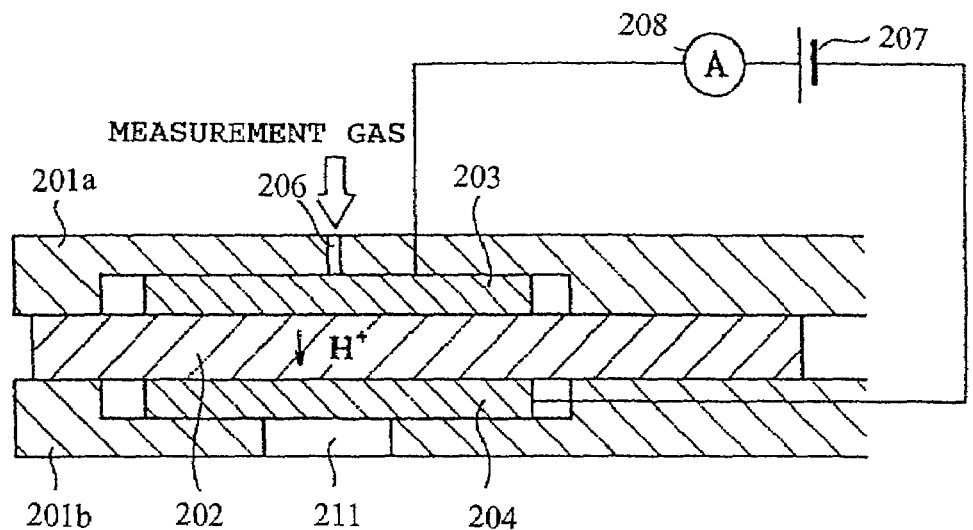
FIG. 4 is a sectional view of a main portion of a gas sensor illustrating the structure of a combustible-gas sensor according to an embodiment of the present invention.

FIG. 4 is a sectional view of a main portion of a gas sensor illustrating a combustible-gas sensor according to a first embodiment of the present invention. Referring to FIG. 4, the combustible-gas sensor is configured such that a first electrode 203 and a second electrode 204 are formed in opposition to each other with a proton conductive layer 202 being held therebetween. The first electrode 203 and the second electrode 204 are in contact with the proton conductive layer 202. The first electrode 203, the proton conductive layer 202, and the second electrode 204 are held between an upper support element 201a and a lower support element 201b, which constitute a support element. A gas diffusion controlling portion 206 for introducing a measurement gas onto the first electrode 203 is formed in the upper support element 201a. A hole 211 is formed in the lower support element 201b, in contact with the second electrode 204. A power supply 207 and an ammeter 208 are connected between the first electrode 203 and the second electrode 204 via lead portions, thereby enabling application of voltage and measurement of current.

The proton conductive layer 202 is formed of Nafion (trademark, product of DuPont), which is a fluorine-containing resin which operates at relatively low temperature. Each of the first electrode 203 and the second electrode 204 is a porous electrode which is made of carbon or the like and carries a catalyst, such as Pt, on the side in contact with the proton conductive layer 202. The insulating support element (the upper support element 201a and the lower support element 201b) is formed of a ceramic such as alumina. Notably, the support element can be formed of a resin or a like material. The gas diffusion controlling portion 206 is formed of gas-permeable, porous alumina. Notably, when the combustible gas contained in a measurement gas is hydrogen, the gas diffusion controlling portion 206 may be formed of a very fine through-hole having a diameter of about 30 to 450 μm. The proton conductive layer 202, the first electrode 203, and the second electrode 204 are physically held in the support member, in contact with one another. Notably, the proton conductive layer 202, the first electrode 203, and the second electrode 204 may be bonded together by use of a hot pressing process.

Next, the principle of measuring the concentration of hydrogen gas (an example combustible gas) by use of the above-described combustible-gas sensor is described with reference to FIG. 4.

(1) Hydrogen gas contained in a measurement gas which has reached the first electrode 203 through the gas diffusion controlling portion 206 is dissociated into protons by the catalytic action of Pt or a like catalyst contained in the first electrode 203 and the voltage applied between the first electrode 203 and the second electrode 204, thereby generating protons.

(2) The generated protons are pumped out toward the second electrode 204 through the proton conductive layer 202 and again become hydrogen gas. The hydrogen gas diffuses into the measurement gas atmosphere via the hole 211.

(3) At this time, the current flowing between the first electrode 203 and the second electrode 204 is proportional to the concentration of hydrogen gas in the measurement gas if the applied voltage is sufficiently high for the current to reach limiting current. Therefore, on the basis of the current (limiting current), the concentration of hydrogen gas in the measurement gas can be obtained.

Measurement Example 10

The concentration of hydrogen gas (example combustible gas) contained in a measurement gas was measured by use a plurality of combustible-gas sensors which have a sensor structure as shown in FIG. 4, and which have the same EW value, but differ from one another in thickness of the proton conductive layer. In the measurement, a predetermined voltage was applied between the first and second electrodes, and the current flowing between the first and second electrodes was measured so as to determine the hydrogen gas concentration. For the measurement, perfluorosulfonic acid films of different thicknesses were used. The thicknesses are as follows: (1) 0.029 mm, (2) 0.080 mm, (3) 0.185 mm, (4) 0.346 mm, (5) 0.577 mm. Notably, each thickness was measured by use of a micrometer in the atmosphere (20° C., RH: 30%). Other conditions are specified below.

Figure 5:
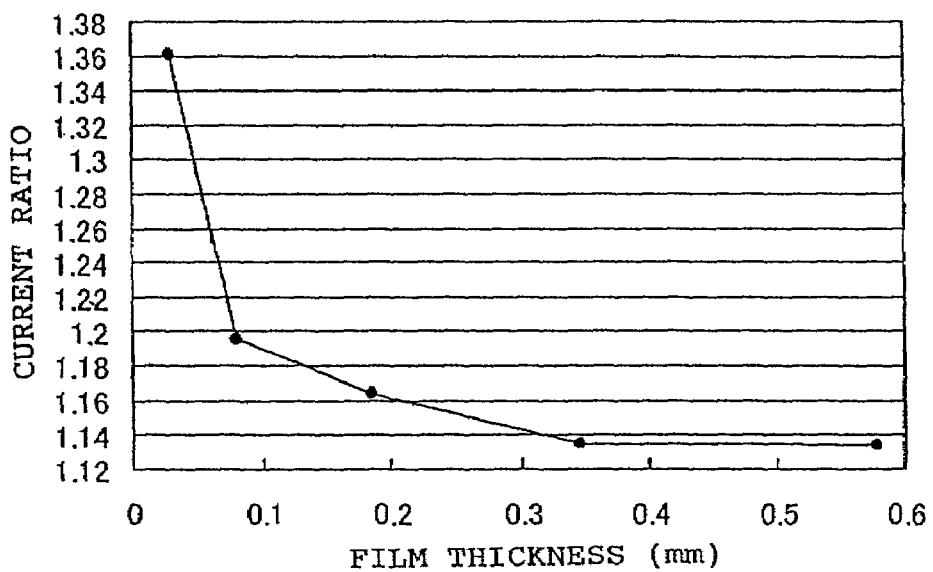
FIG. 5 is a graph for showing he results of Measurement Example 1.

<Measuring Conditions>
   Measurement gas composition: 50% $H_2$, 15% $CO_2$, 10, 30% $H_2O$, balance $N_2$
   Measurement gas temperature: 80° C.
   Measurement gas flow rate: 10 L/min
   Voltage Vp applied between the first and second electrodes: 400 mV FIG. 5 is a graph for explaining the results of Measurement Example 10. In FIG. 5, the horizontal axis represents the thickness of the proton conductive layer, and the vertical axis represents current ratio. Current ratio is a ratio of current flowing between the first and second electrodes when $H_2O$=30% to current flowing between the first and second electrodes when $H_2O$=10%.

As can be seen from FIG. 5, the current ratio decreases when the proton conductive layer has a thickness of not less than 0.08 mm. This result demonstrates that the $H_2O$ concentration dependency of hydrogen-gas concentration measurement can be mitigated through employment of a polymer electrolyte film having a thickness of not less than 0.08 mm. Further, it is understood that a predetermined characteristic can be obtained when the thickness is set to 0.08 mm to 0.6 mm.

Example 11

A combustible-gas sensor according to the another embodiment of the present invention has the same sensor structure as that of the combustible-gas sensor according to Example 10 (see FIG. 4) and has a proton conductive layer which is formed of a polymer electrolyte, protons of ion exchange groups of the polymer electrolyte having been partially substituted by metal ions. Specifically, a film of Nafion 117 (EW=1100) was subjected to an ion substitution process by use of sodium ions, and the combustible-gas sensor according to the second embodiment was fabricated by use of the film as a proton conductive layer. An example metal-ion substitution process will be shown below.

[1] Boiling in 3% hydrogen peroxide solution (for removal of organic contaminants): 1 hour.
[2] Boiling in distilled water: 1 hour.
[3] Boiling in aqueous solution containing sodium sulfate at a concentration of $1\times10^{-3}$ mol/L: 1 hour.
[4] Boiling in distilled water: 1 hour.

Notably, when protons of ion exchange groups of the proton conductive layer are partially substituted by metal ions by the above-described metal ion substitution process, the ion exchange group capacity decreases. Particularly, when the ion substation process was performed for the above-described Nafion 117 film (EW=1100) by means of sodium ions, the film attained an EW value greater than 1100.

Measurement Example 11

The concentration of hydrogen gas (an example combustible gas) contained in a measurement gas was measured by use of the combustible-gas sensor according to Example 11. In the measurement, a predetermined voltage was applied between the first and second electrodes, and the current flowing between the first and second electrodes was measured so as to determine the hydrogen gas concentration. Other conditions are specified below.

Figure 6:
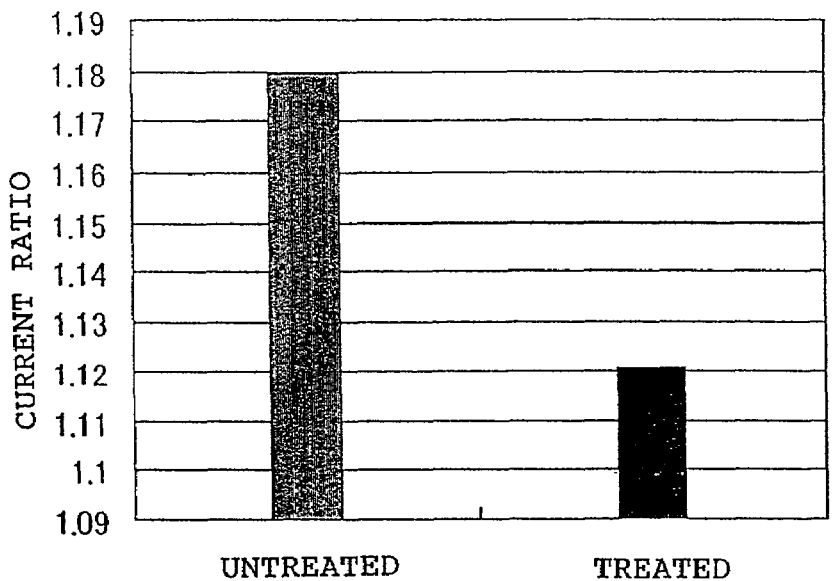
FIG. 6 Is a graph showing the results of Measurement Example 3.

<Measuring Conditions>
   Measurement gas composition: 50% $H_2$, 15% $CO_2$, 10, 30% $H_2O$, balance $N_2$
   Measurement gas temperature: 80° C.
   Measurement gas flow rate: 10 L/min
   Voltage Vp applied between the first and second electrodes: 400 mV FIG. 6 is a graph for explaining the results of Measurement Example 11. The current ratio of the vertical axis is a ratio of current flowing between the first and second electrodes when $H_2O$=30% to current flowing between the first and second electrodes when $H_2O$=10%.

As can be seen from FIG. 6, the current ratio decreases when the above-described ion substitution process is performed. This result demonstrates that the $H_2O$ concentration dependency of hydrogen-gas concentration measurement can be mitigated through a process of partially substituting protons of ion exchange groups of the proton conductive layer by metal ions.

Measurement Example 12

Measurement was performed in order to determine preferred conditions for the above-described ion substitution process for the proton conductive layer. Specifically, the above-described ion substitution process was performed by use of aqueous sodium solutions of different concentrations, and the impedance between the first and second electrodes was measured by use of an impedance analyzer under the following conditions.

Concentration of aqueous sodium sulfate solution used for the ion substitution process: $1\times10^{-4}$ mol/L, $1\times10^{-3}$ mol/L, $1\times10^{-2}$ mol/L Measured atmosphere: 20° C., RH: 30%, air Measurement conditions of the impedance analyzer: frequency: 5,000 Hz, voltage applied between the first and second electrodes: 150 mV Results of Measurement Examples 12 are shown in Table 2 below.

TABLE 2

| Processing concentration (mol/L) | Results |
|---|---|
| $1\times10^{-2}$ | Conductivity Not established |
| $1\times10^{-3}$ | Conductivity established |
| $1\times10^{-4}$ | Conductivity established |

Table 2 shows that the impedance between the first and second electrode becomes excessively high when the concentration of sodium ions is $1\times10^{-2}$ mol/L or greater. This test result demonstrates that the concentration of an aqueous sodium solution used for the substitution process is preferably set to be less than $1\times10^{-2}$ mol/L, and more preferably to not greater than $1\times10^{-3}$ mol/L Example 12

Next, a combustible-gas sensor according to still another embodiment of the present invention is described. The structure of the combustible-gas sensor according to this embodiment differs from that of the combustible-gas sensor according to Example 10 in that a reference electrode is added. The following description of the embodiment of Example 12 mainly covers the difference between Example 12 and Example 10. For structural features of the combustible-gas sensor according to the third embodiment that are similar to those of the combustible-gas sensor according to the first embodiment, the description of the first embodiment may be referred to as appropriate.

Figure 7:
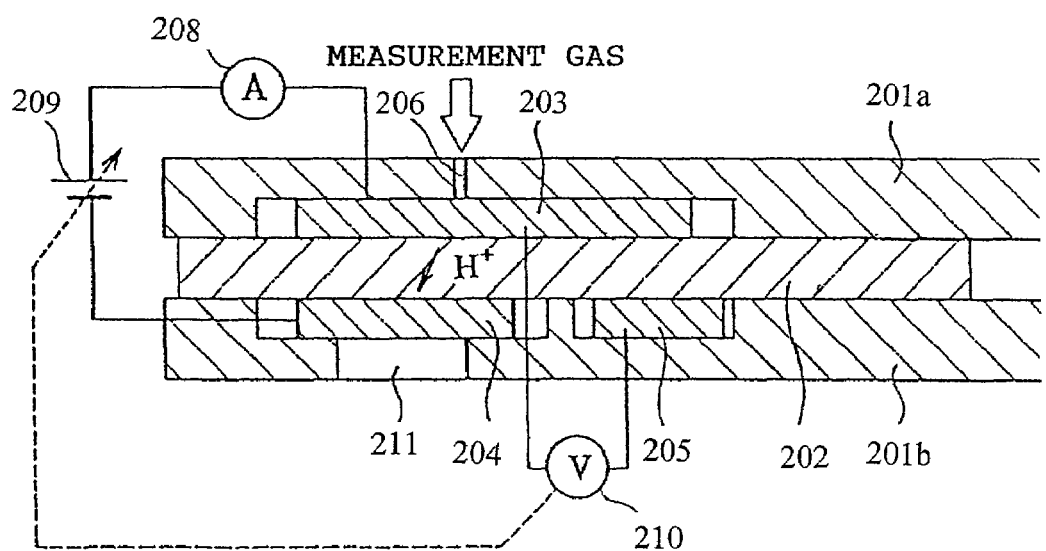
FIG. 7 is a sectional view of a main portion of a gas sensor illustrating the structure of a combustible-gas sensor according to a preferred embodiment of the present invention.

FIG. 7 is a sectional view of a main portion of a gas sensor illustrating the structure of the combustible-gas sensor according to the third embodiment of the present invention. Referring to FIG. 7, this combustible-gas sensor is configured such that a reference electrode 205 is formed in contact with the proton conductive layer 202. The reference electrode 205 is covered with the support element 201b so as to reduce the influence of variation in the concentration of combustible gas in a measurement gas. The reference electrode 205 and the second electrode 204 are formed on the same surface of the proton conductive layer 202 and disposed in different chambers.

In order to further stabilize the combustible gas concentration on the reference electrode 205, the reference electrode 205 is preferably a self-generation-type reference electrode. This can be attained in the following manner: a constant, very small current is caused to flow from the first electrode 203 to the reference electrode 205 such that a portion of the combustible gas leaks, in the form of hydrogen, to the exterior of the sensor via a predetermined leakage resistance portion (e.g., a very fine hole).

A potentiometer 210 is connected between the first electrode 203 and the reference electrode 205 via lead portions. A power supply 209 and an ammeter 208 are connected between the first electrode 203 and the second electrode 204 via lead portions. Sufficient voltage is applied between the first electrode 203 and the second electrode 204 such that the electric potential difference between the first electrode 203 and the reference electrode 5 assumes a constant value. At this time, the current flowing between the first electrode 203 and the second electrode 202 is measured.

Next, the principle of measuring the concentration of hydrogen (an example combustible gas) by use of the above-described combustible-gas sensor will be described with reference to FIG. 7.

(1) Hydrogen gas which has reached the first electrode 203 through the gas diffusion controlling portion 206 generates an electromotive force, according to its concentration, between the first electrode 203 and the reference electrode 205 via the proton conductive layer 202.

(2) Voltage is applied between the first electrode 203 and the second electrode 204 such that hydrogen gas concentration on the first electrode 203 becomes constant; i.e., the electric potential difference between the first electrode 203 and the reference electrode 5 becomes constant.

(3) As a result, hydrogen gas is dissociated into protons on the first electrode 203. The thus-generated protons are pumped out toward the second electrode 204 through the proton conductive layer 202 and again become hydrogen gas. The hydrogen gas diffuses into the measurement gas atmosphere.

(4) At this time, the current flowing between the first electrode 203 and the second electrode 204 is proportional to the concentration of hydrogen gas in the measurement gas. Therefore, on the basis of the current, the concentration of hydrogen gas in the measurement gas can be obtained.

The combustible-gas sensor according to the foregoing embodiment of the present invention can control the concentration of hydrogen gas on the first electrode to a constant level while the voltage applied between the first electrode and the second electrode is optimally varied according to the concentration of hydrogen in the measurement gas—high voltage is applied at high concentration, and low voltage is applied at low concentration—such that the electric potential difference between the first electrode and the reference electrode becomes constant.

Even when resistance between the first electrode and the second electrode increases because of variation in, for example, the temperature of the measurement gas, the combustible-gas sensor according to the third embodiment of the present invention can control the concentration of hydrogen gas on the first electrode to a constant level by varying the applied voltage as appropriate. Thus, by setting the electric potential difference between the first electrode and the reference electrode to the optimum value, this combustible-gas sensor can always control hydrogen concentration on the first electrode to not less than $10^{-12}$ atm as reduced to partial pressure of hydrogen, even when used in an atmosphere whose hydrogen gas concentration, temperature, etc. vary greatly. Therefore, even when methanol is present, combustible gas concentration can be accurately measured over a wide concentration range without being influenced by methanol.

From the foregoing, it is seen that the present invention provides a combustible-gas sensor which is not affected by variation in $H_2O$ concentration of an atmosphere.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A gas sensor for measuring a hydrogen concentration of a gas atmosphere containing $H_2$ and $H_2O$, comprising a proton-conductive polymer electrolyte layer, a first electrode and a second electrode formed in contact with the proton-conductive polymer electrolyte layer and sandwiching the proton conductive polymer electrolyte layer, a partition wall provided between the first electrode and the gas atmosphere to be measured, and a diffusion-controlling hole provided in the partition wall and extending through the partition wall between the first measuring electrode and the gas atmosphere to be measured, the gas sensor being characterized in that $A/(B \times C)$ is not less than $9.5 \times 10^{-5}$ mm$^{-1}$, where A (mm$^2$) is an opening area of the diffusion-controlling hole on a side toward the gas atmosphere to be measured, B (mm) is a length of the diffusion-controlling hole, and C (mm$^2$) is an area of the first electrode or that of the second electrode, whichever is smaller and wherein $I_{30}/I_{20}$ is less than 1.2, where $I_{30}$ is a limiting current as measured with an atmosphere to be measured which contains $H_2$ in an amount of 50% by volume and $H_2O$ in an amount of 30% by volume, and $I_{20}$ is a limiting current as measured with an atmosphere to be measured which contains $H_2$ in an amount of 50% by volume and $H_2O$ in an amount of 20% by volume.

2. The gas sensor as in claim 1, wherein the proton-conductive polymer electrolyte layer is formed of a polymer electrolyte having a thickness of not less than 0.08 mm.

3. A method for measuring gas concentration, comprising measuring a limiting current flowing between the first electrode and the second electrode by use of the gas sensor as in claim 1.

4. A gas sensor as in claim 1, further comprising a reference electrode bonded to the polymer electrolyte layer.

5. A method for measuring gas concentration, comprising measuring a limiting current flowing between the first electrode and the second electrode by use of the gas sensor as in claim 4.

6. A method for measuring gas concentration, wherein a limiting current flowing between the first electrode and the second electrode is measured by using the gas sensor as in claim 4 while voltage is applied to the first electrode and the second electrode such that the voltage as measured between the first electrode and the reference electrode becomes constant.

7. A method for measuring gas concentration, comprising measuring a limiting current flowing between the first electrode and the second electrode by use of the gas sensor as in claim 1.

8. The gas sensor as in claim 1, further comprising a reference electrode provided in contact with the proton-conductive layer, wherein a predetermined voltage is applied between the first electrode and the second electrode in such a manner as to establish a constant electric potential difference between the first electrode and the reference electrode.

9. The gas sensor as in claim 1, wherein the gas to be measured is hydrogen.

* * * * *